(12) United States Patent
Dalgaard et al.

(10) Patent No.: US 7,316,652 B2
(45) Date of Patent: Jan. 8, 2008

(54) BLOOD PRESSURE MEASURING DEVICE WITH A CUFF OF TWO OPENABLE CONCAVE SHELL PARTS

(75) Inventors: Torben Dalgaard, Holstebro (DK); Niels Toft Jorgensen, Loesnig (DK)

(73) Assignee: Bang & Olufsen Medicom A/S, Struer (DK)

( * ) Notice: Subject to any disclaimer, the term of this patent is extended or adjusted under 35 U.S.C. 154(b) by 0 days.

(21) Appl. No.: 10/502,325

(22) PCT Filed: Jan. 23, 2003

(86) PCT No.: PCT/DK03/00041

§ 371 (c)(1),
(2), (4) Date: May 20, 2005

(87) PCT Pub. No.: WO03/061468

PCT Pub. Date: Jul. 31, 2003

(65) Prior Publication Data

US 2005/0228302 A1    Oct. 13, 2005

(30) Foreign Application Priority Data

Jan. 23, 2002    (DK) .............................. 2002 00121

(51) Int. Cl.
*A61B 5/02*    (2006.01)
(52) U.S. Cl. ............. 600/499; 600/485; 600/490
(58) Field of Classification Search ........... 600/499
See application file for complete search history.

(56) References Cited

U.S. PATENT DOCUMENTS

| | | | |
|---|---|---|---|
| 4,058,117 A * | 11/1977 | Kaspari et al. | 600/495 |
| 4,248,241 A * | 2/1981 | Tacchi | 600/484 |
| 4,248,242 A | 2/1981 | Tamm | |
| 4,337,778 A | 7/1982 | Akira et al. | |
| 4,790,325 A * | 12/1988 | Lee | 600/490 |
| 5,025,793 A | 6/1991 | Richley et al. | |
| 5,031,630 A * | 7/1991 | Hirano et al. | 600/493 |
| 5,201,320 A | 4/1993 | Barker | |
| 5,421,341 A | 6/1995 | Marangoni | |
| 5,560,365 A | 10/1996 | Ogura | |
| 2002/0107450 A1 * | 8/2002 | Ogura | 600/490 |

* cited by examiner

*Primary Examiner*—Charles A. Marmor, II
*Assistant Examiner*—Patricia C. Mallari
(74) *Attorney, Agent, or Firm*—David S. Safran

(57) ABSTRACT

Traditional cuffs for measuring blood pressure use an air chamber enclosed in a non-stretchable fabric to occlude an artery in a limb when supplied with pressurised air. A stethoscope used on the limb is used to monitor blood flow. Application of the cuff is inconvenient and correct placement of the stethoscope chestpiece requires skill. According to the invention blood pressure measurement is facilitated by having the air chamber enclosed in a pre-formed shell-like structure being flexible around the limb and stiff along the limb and by using a linear array of microphones to detect the blood flow noises, the best signal from one of the microphones being automatically selected. Furthermore, the invention provides a facility for correcting the reading in dependence of the amount of wrap of the limb.

23 Claims, 4 Drawing Sheets

BLOOD PRESSURE MEASURING DEVICE WITH A CUFF OF TWO OPENABLE CONCAVE SHELL PARTS

Figure 1:
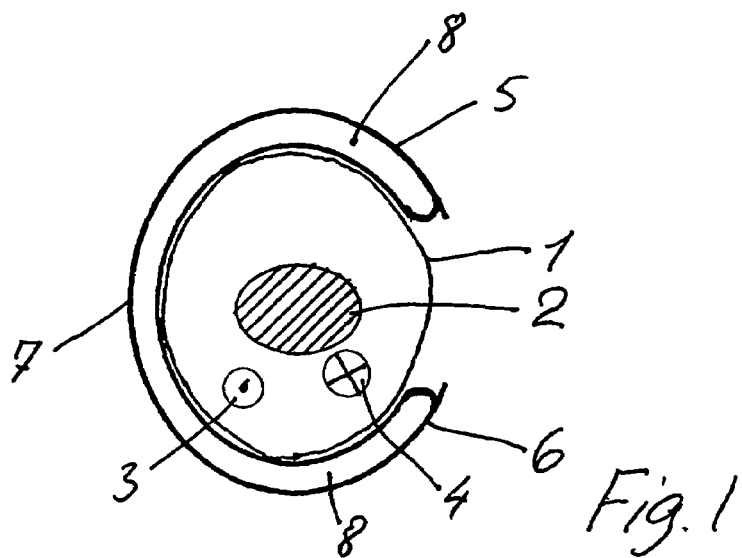

The invention concerns apparatus for measuring blood pressure, comprising a generally tubular constrictable sleeve or cuff for a limb of a person, a source for fluid pressure, means for measuring static pressure, and microphone means arranged in proximity to an artery.

Modern blood pressure measurements have long traditions and fall into two distinct types. Both the auscultatory and the oscillometric method use the constriction of an artery to such a degree that blood flow is stopped and then allowed to flow while a signal derived from the blood pressure is monitored. The constriction occurs by means of a cuff surrounding a limb (in most cases an upper arm or a wrist). The cuff has a non-stretchable fabric on the outside enclosing an elongate bladder surrounding a large part of the limb periphery. The bladder is pressurised by means of air, and the air pressure is monitored. The Korotkoff method depends on listening to sounds in the artery downstream of the constriction as blood begins to flow, and to read the pressure when certain sounds related to the heartbeat are heard and again when sounds begin to disappear. Traditionally, the listening has occurred by means of a stethoscope, the chestpiece of which is held against the skin in proximity to the artery downstream from the occlusion, frequently supported against the edge of the cuff.

The above process of measuring blood pressure is perceived as a slow process and one which requires skill. This is due to the manipulation, requiring two hands, involved in fitting the cuff, and the need for precise placement of the stethoscope chestpiece. The pumping and release of air are perceived as the least time consuming, particularly because they pertain to the actual measurement. Modem measurement methods use automatic pumping and release and electronic microphone pickup of the Korotkoff sounds and possibly some signal processing aids in distinguishing between the various types of sound.

U.S. Pat. No. 4,337,778 describes an attempt to reduce the entanglement of air tube and microphone lead in connection with the wrapping and unwrapping of the cuff, in that the Korotkoff sounds are picked up by means of a microphone inside the inflatable bladder. However, the patent does not attempt to solve the fundamental time-consuming problem of the wrapping and unwrapping for the single-handed individual.

In U.S. Pat. No. 5,560,365 it is described how the provision of a partially stretchable cuff may reduce friction noises in case the blood pressure measurement is performed on a non-stationary limb. It improves the signal to be analysed, but it does not solve the problem of fitting the cuff.

In U.S. Pat. No. 4,248,242 it is described how a blood pressure apparatus may be semi-automated by means of a sequential switch and hand pump arranged on apparatus integrated with the cuff The cuff itself still has to be threaded on the arm. A sensor is provided for picking-up the Korotkoff sounds but there is no indication of the manner in which it is fitted to the apparatus.

U.S. Pat. No. 4,790,325 relates to an automatic blood pressure recorder, in which the patient is required to sit and place his arm in a solid fixture or jig integrated into an armrest and containing inflatable elements, said fixture being closed automatically by an equally solid clamp. This makes the equipment very stationary and ill suited for patients unable to sit upright in a chair-like construction.

It is hence an object of the invention to provide a cuff-and-microphone combination that is able to provide consistent good acoustic coupling and signal processing to obtain dependable artery sound signals. It is a further object of the invention to provide a cuff structure that is adaptable to a wider range of biometric measures of a limb than known apparatus. It is a still further object of the invention to provide an indication of a mismatch in case the biometric measurements serviced reliably by the cuff fall outside the limits of its adaptability and to propose a correction commensurate with the mismatch.

According to the invention the above deficiencies are avoided and the advantages obtained, in that the cuff is at least partly enclosed in two essentially concave shell parts displaying a stiffness along the limb, said shell part being openable against a restoring force, and in that a linear array of microphone elements is disposed on a universal joint type support in one shell part essentially perpendicular to the longitudinal axis of such shell part and near the lower end. The term "concave" refers to the fact that the shell parts may be straight axially along the arm, whereas they intendedly curve in the direction perpendicular to the axial direction along the arm. The term "stiffness" refers to the fact that it is not intended to give the shell a curvature in the axial direction that deviates from any curvature it may have been given during manufacture. A universal joint type support for a linear array perpendicular to an axis is characterised by permitting movement in a plane perpendicular to said axis as well as rotation about an axis along the linear array. There is a distinct advantage to using a stiff shell for enclosing the inflatable cuff, rather than the traditional woven strap, because the forces between the cuff and the limb (upper arm) are more evenly distributed and so facilitate a stable and repeatable occlusion of the artery. This is important both for the auscultatory and for the oscillometric method. In case of the auscultatory method the rotational precision required in fitting the implement is much reduced by providing several microphones in combination with the stiff shell, because it will at all times be possible to find the microphone which provides the clearest signal. There is a particular advantage to using such an array of microphones when the inflated cuff is retained by a stiff shell, because the repeatability of fitting the apparatus and of the readings are hugely increased. The implement may be entirely supported by a limb, i.e. without attachment to constructive elements carried by e.g. an arm rest.

According to an advantageous embodiment signal selection means of the diversity reception type are used to select the microphone that provides the best signal-to-noise ratio. Rather than averaging the output of the linear array of microphones it is much more efficient to select the microphone which at the same time receives the strongest signal but also the least amount of extraneous noise.

According to a further advantageous embodiment the microphone signal is amplified and made available to an electroacoustic converter for enabling listening to the signal. This means that an examining physician may demonstrate to others, including the patient, the character of the Korotkoff sounds directly from the apparatus of the invention, rather than from a separate stethoscope.

According to a further advantageous embodiment the signal is output via a built-in speaker in the apparatus. This makes the apparatus completely self-contained.

According to a further advantageous embodiment the signal is output via a wireless link to a receiver connected to earpieces carried by an auscultating physician. Such a receiver/earpiece combination may typically be a part of an electronic stethoscope already carried by the physician and other medical staff surrounding the person whose blood pressure is measured by the present apparatus.

A further advantageous embodiment of the invention is particular in that it comprises signal processing means for combining information derived from measurements of slowly varying static pressures with information from said microphone means in order to obtain a numerical value for a blood pressure. This would typically include cycling the static pressure and obtaining a sound signal in dependence thereof, the frequency content of said signal determining the type of Korotkoff sound detected, and sampling said static pressure and combining with frequency content signatures sampled essentially simultaneously therewith will provide numerical information of the pressures required to obtain specific Korotkoff type sounds.

According to a further advantageous embodiment an inelastic strap attached to one shell part is provided to close the gap between the shell parts. The use of a strap is known per se from traditional cuffs, however, according to the invention its action is more consistent because it attaches the shell parts.

According to a further advantageous embodiment the strap is provided with means locking to the other shell part in conjunction with the overlapping of said strap and said other shell part. Such means would be of a quick-release type.

According to a further advantageous embodiment the amount of overlap between the strap and the shell is used as a circumference measure for automatically correcting the reading of blood pressure. It is well known that for a constant circumference of the cuff fitted snugly to a limb, the precision to which the systolic and diastolic pressures are given depends on the axial dimension of the cuff. The length of the implement according to the present invention being constant and precise, due to the stiffness of the shell, knowledge of the circumference enables a suitable correction to be applied to the reading. The absolute value of the circumference is equal to the circumference of the cuff plus the contribution of the flap. The correction is performed during the signal processing in dependence of the overlap signal from the strap. The skilled person will choose any of several technologies available for this kind of relative position measurement. Hence the need for several sizes of cuffs known from traditional blood pressure measuring setups is reduced.

According to a further advantageous embodiment the overlap is measured capacitively between an electrode or a plurality of electrodes fixed to the cuff and an electrode or a plurality of electrodes fixed to the strap. A capacitive detection and capacitive transmission of measurement data is well suited for a blood pressure measuring implement, which may use disposable parts, because expensive and time-consuming plug-and-socket connections are avoided.

According to an advantageous embodiment the shells are fitted on a hinge connected to handle parts operable by one hand. This in effect means that correct placement of the implement is possible using one hand only, whereby a person may use the implement on himself.

According to a further advantageous embodiment in addition to a stiffness in the longitudinal direction the shell structure displays a resilience in the circumferential direction. In this manner, the shell will adapt still closer to the limb when it is gripping it.

According to a further advantageous embodiment the hinge is a continuous resilient part joining the shell parts. It is important that the shells fits closely to the tissue when the implement is fitted, and the handles act against the force of such a resilient part.

According to a further advantageous embodiment the shell parts are integral with the hinge part, forming one continuous sheet of material. This means that the implement may be manufactured in one piece which is given its proper shape during manufacture. An example of this continuous sheet structure for the shell parts may be envisaged, in which the resilience in the circumferential direction is actually an extreme "limpness". Integral shell parts in the form of a woven sheet having flexible but generally unstretchable strings as the warp and a number of parallel, stiff strips as the weft would be oriented on a limb so that the weft direction would be parallel to the axis of the limb.

According to a further advantageous embodiment the continuous sheet of material assumes a generally frusto-conical shape in its closed state. This may require a "pre-distortion" of the shape of the implement and would be most practical in connection with well-developed muscles in the upper arm. However, it has been determined that in connection with the shell-type construction according to the invention the frusto-conical shape of the implement has a larger range of adaptation to biometrical measurements than a cylindrical type.

According to a further advantageous embodiment mechanical actuating means fitted in proximity to the hinge part compress one shell part towards the other during measurement. In case the implement is to be used by persons having too little strength in the actuating hand, the opening of the shell parts by means of the handles may be made to require only a small force. However, in this case some mechanical assistance is required to compress the two shells towards each other prior to fitting a strap and measurement.

According to a further advantageous embodiment the mechanical actuating means consist of an air cylinder and levers. Air under pressure is available for inflating the air chambers of the cuff, and hence a suitable actuating means for the shell parts would be an air cylinder or another closed shape-changing vessel.

According to a further advantageous embodiment the mechanical actuating means consist of strings fitted near the inner side of each shell part and disposed perpendicular to the longitudinal axis of such shell part. This will give an action similar to the action of the tendons in a hand when closing it into a fist. This type of actuation is more adapted to electric power, because the strings may be tightened by winding them on a rotating shaft.

According to an embodiment of the invention an inflatable cuff forms an inner lining to the shell parts, providing an inflatable main air chamber. With the secure support of the shell parts it is possible to obtain a secure and repeatable inflation, without any distortion of the air chamber that could lead to difficulties in occluding the blood vessels.

According to a further advantageous embodiment the strap is provided with air chambers disposed essentially perpendicular to the orientation of the shells and communicating with the main air chamber. This in effect means that an inflatable structure surrounds the whole arm, again providing improved repeatability in inflation.

According to a further advantageous embodiment the universal joint is emulated by a foam pad. This is an efficient manner to provide a support for the microphone array or bridge, both from a manufacturing viewpoint and because the resilience of the foam pad may be adjusted in correspondence to the length of the bridge, thickness of the microphone elements, etc. A foam pad will permit certain deviations from the perpendicular position of the microphone bridge, i.e. permit a closer fit to the skin when so required.

According to a further advantageous embodiment the universal joint is emulated by means of a separate air chamber fitted between the cuff and the microphone array. This means that the contact pressure of the microphone bridge may be adjusted during measurement, if required.

One use of the apparatus is for an upper arm, in which the possibility of using only one hand for fitting it makes it entirely practical for a patient to monitor blood pressure without assistance from medical personnel.

A further use of the apparatus is for a leg, in particular in cases where injuries to the upper torso prevent the measurements on arms. The dimensions of the implement in question must generally be larger than for an arm, however even in this case, the precise location of an artery is not required, as the advantages of using a microphone array in combination with a shell structure would still manifest themselves.

Figure 2:
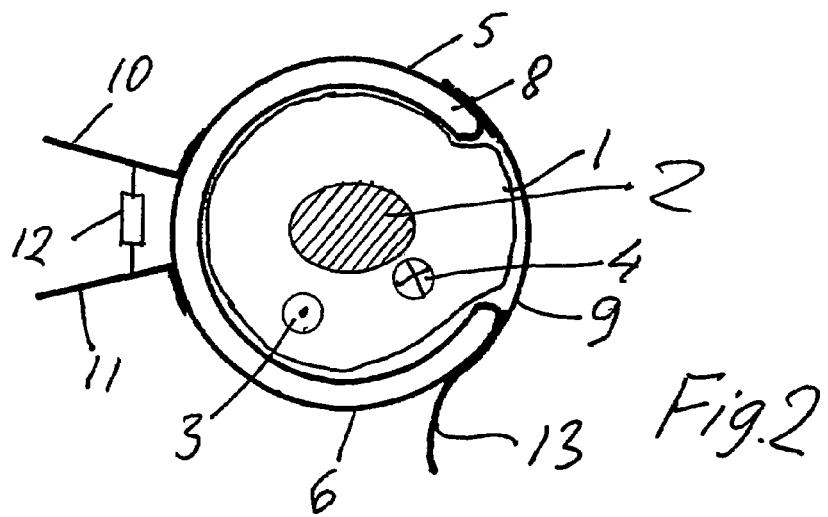
Figure 3:
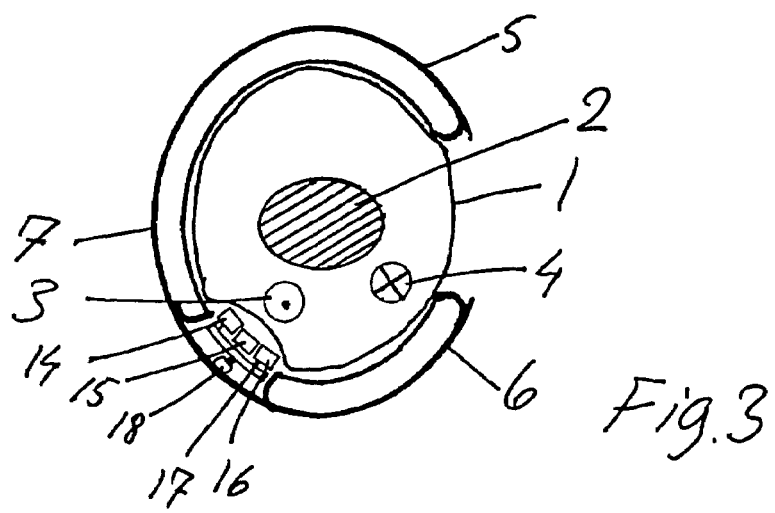
Figure 4:
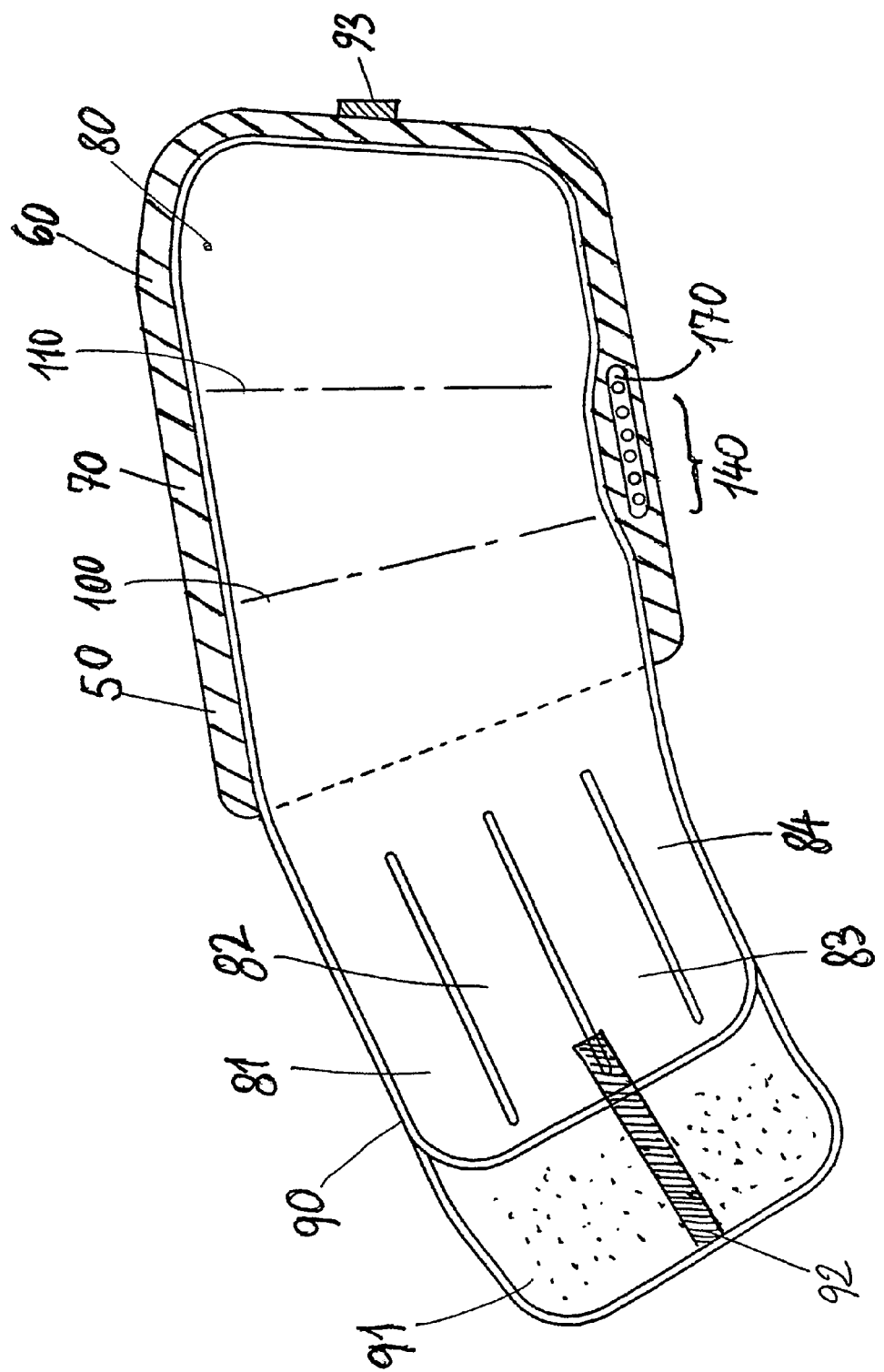
Figure 5:
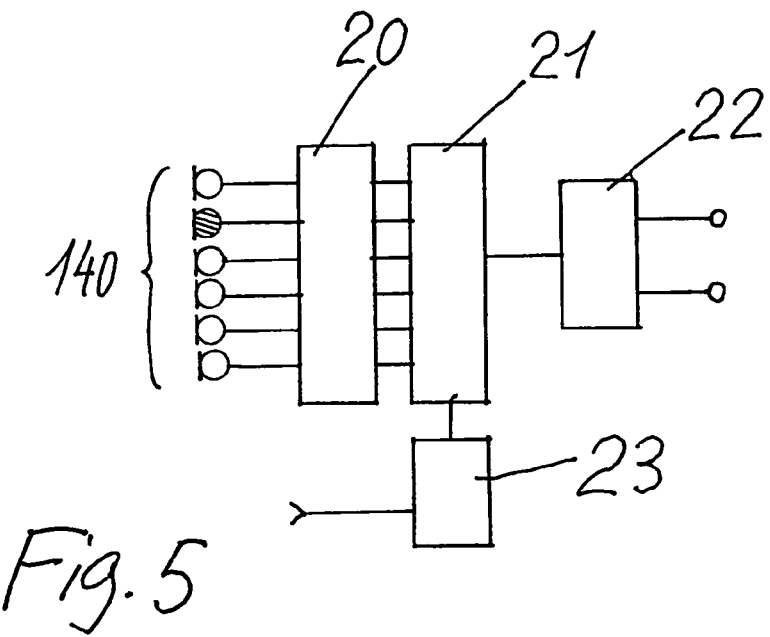
Figure 6:
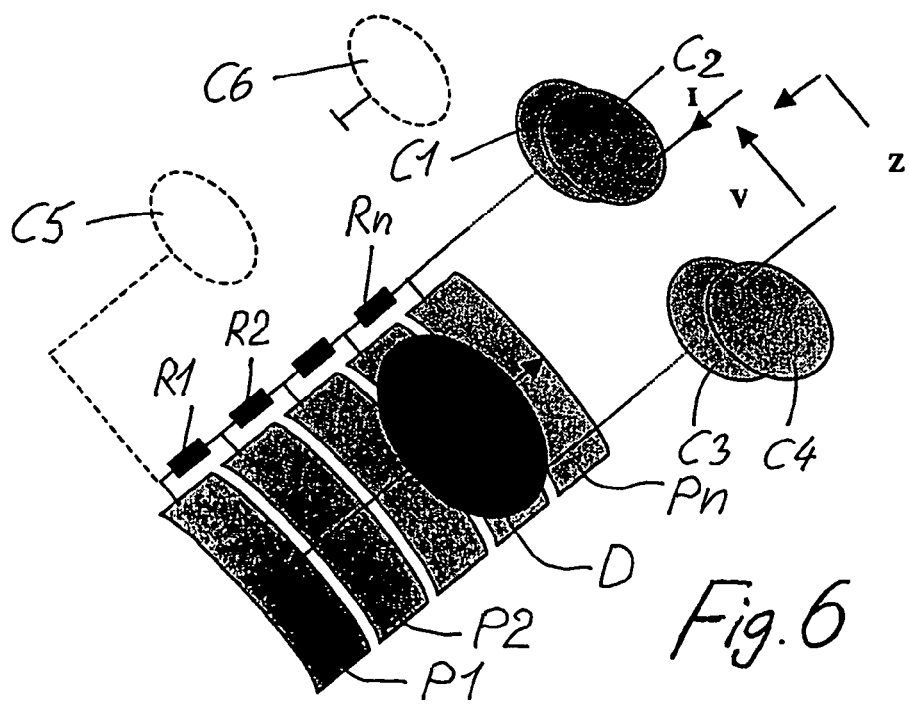
Figure 7:
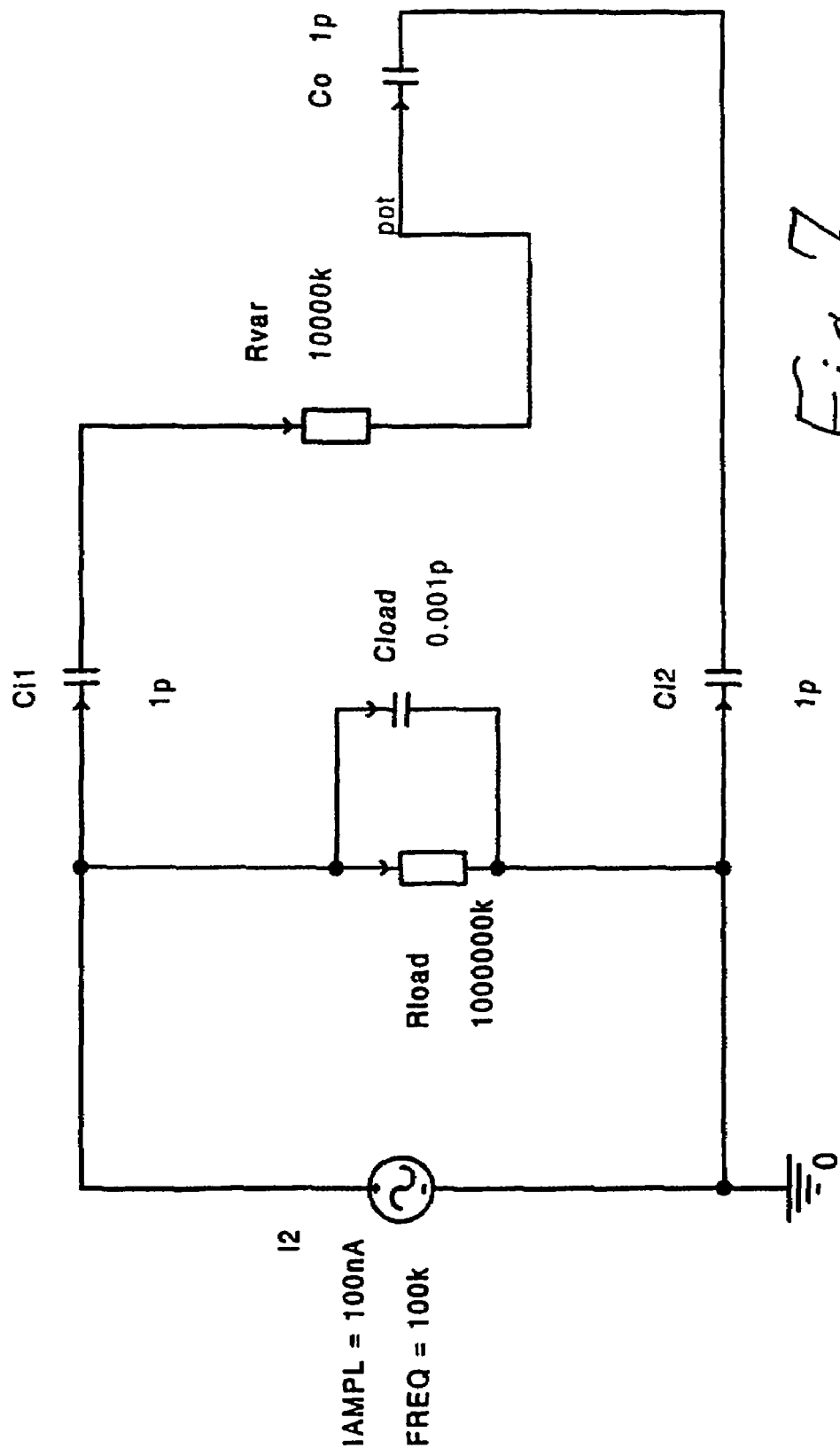

The invention will be more fully described in the following with reference to the drawing, in which:

FIG. 1 shows a first cross section through one embodiment of the invention fitted to a limb, FIG. 2 shows a second cross section, further along the limb, FIG. 3 shows a third cross section, still further along the limb, FIG. 4 shows another embodiment of the invention, seen from the inside, FIG. 5 shows signal processing means for selecting a signal with a good signal-to-noise ratio, FIG. 6 shows one embodiment of a capacitive overlap detector, and FIG. 7 shows the electrical equivalent circuit of such a detector.

In FIG. 1 there is shown a cross section through a limb around which the inventive implement is fitted. Purely by way of example this is to be considered as an upper left arm extended horizontally forwards with respect to a vertical torso. The arm 1, the bone 2, an artery 3 and a vein 4 are indicated. The arm 1 is enclosed in a shell-like structure consisting of an upper part 5 and a lower part 6, connected by a part 7.

The parts are made of a material which is pliable around the arm but stiff in its longitudinal direction. To the inside of parts 5, 6, 7 is fitted an inflatable structure 8 which is able to compress the tissue of the arm 1 around the bone 2, provided the shell-like structure does not increase its outer dimensions.

In FIG. 2 is shown how the outer dimensions of the shell-like structure are maintained. This is obtained in that a strap or flap 9 is connected between the upper part 5 of the shell-like structure and the corresponding lower part 6. The flap is made in a material which does not extend when put under tension, and so the circumference of the inventive implement is constant. When the inflatable structure 8 is inflated, the implement tends towards a shape which provides the largest area for a given circumference which is a circle, and the tissue in the arm 1 is compressed to a degree which may occlude the blood vessels 3 and 4. The implement is fitted with two handle-like structures 10 and 11 which when brought towards each other will increase the distance between the parts 5 and 6, provided the flap 9 has not been connected. A resilient member 12 is acting on the handle structures 10 and 11, attempting to close the shell-like structure 5, 6.

In practical use one hand may act on the handles 10, 11 to open the shell parts 5, 6 in order to fit the implement on the arm 1; in the example above this would be from the right towards the left. The handles 10, 11 are released, the resilient member 12 expands in closing the shell parts 5, 6, and a loose end 13 hanging down from the flap 9 connected to the upper part 5 is gripped from below with the same hand that released the handles and is brought to the right with a pulling motion. The flap 9 attaches itself to the lower part 6 by releasable means, such as the fastener type described in U.S. Pat. No. 2,717,437. The inflatable structure 8 is provided by air under pressure, and the blood vessels are occluded when sufficient pressure has built up.

In FIG. 3 the downstream (looking at the flow in an artery) end of the implement is shown in cross section. This end carries a set of microphones for picking-up signals from the flow in the artery 3. Three microphones 14, 15, and 16 are fitted onto a fixture 17 which is mounted on a universal joint type of bearing 18 in order that the fixture may fit closely to the skin in proximity to the artery 3. In a preferred embodiment the universal joint is emulated by a foam pad. One microphone 16 is shown as being closest to the artery, and the signal from this microphone will have the best signal-to-noise ratio of the three. This is in contrast to a construction embodying an elongate microphone, such as that described in U.S. Pat. No. 4,202,348. While this patent does describe how it is ensured that a signal from an artery is picked up for a range of rotational orientations of the cuff holding the microphone, said construction equally collects various noise signals.

The universal joint type bearing 18 may equally be a small air cushion, not necessarily connected to the main inflatable structure.

In FIG. 4 is shown a different embodiment of the invention, but for clarity it is shown in a form that it would never assume as a finished product. In this case the two shells 50, 60 and the hinge 70 are made of one sheet of material in which the stiffness is dependent on the direction. It is considerably stiffer in its longitudinal direction than cross-wise (around a limb). Such a material may consist of a number of parallel linear structures of increased thickness joined by areas of reduced thickness or may be obtained by corrugation. The upper and lower "shell" parts are pre-formed in a concave shape towards each other, and as in FIG. 2 actuating "handle" parts are able to separate the two "shell" parts, the "hinge" part being equally pre-formed during manufacture. The cross section of this embodiment is similar to FIG. 2, however the general outline of the sheet material is such that it will conform to a frusto-conical shape when the implement is applied.

In FIG. 4 the "shell" and "hinge" parts 50, 60, 70 are shown "flattened" to the image plane. Furthermore is shown the main air chamber 80 lining the sheet of material as well as supplementary air chambers 81, 82, 83, 84 lining the strap or flap 90 which is used to close the implement in a manner described in connection with FIG. 2. The communicating air chambers may advantageously be made in a flexible weldable poly-urethane sheet material. The position of handles 100 and 110 is indicated by dot-dash lines. It will be obvious to the skilled person that the orientation of the flap 90, i.e. whether the closing movement is upwards or downwards is immaterial to the construction, although it may be important to the user. The closing occurs by means of fasteners 91 co-operating with corresponding fasteners on the outside of the part 60 of the implement. The bridge 170 carrying the microphones 140 is shown adjacent to the air chamber 80.

Upper arms being very different in a population, there may be a need for different sizes of implement, however the implement according to the invention will adapt to many biometrical dimensions, the basic frusto-conical shape being adaptable to create even a cylindrical cuff if required. However, the provision of supplementary air chambers in the flap itself enables a larger range of upper arms to be measured with one and the same implement, than for known cuffs.

The strap 90 and its fastening flap 91 for joining to the outside of the shell 60 are provided with extension measuring means 92, 93 which are able to provide a signal indicating the amount of overlap of the strap when fitted to the limb. The overlap is used as a measure representing the degree of encirclement of the arm by the inflatable part. It has been determined that for reliable readings, the inflatable part must encircle ca. 80% of the arm. Furthermore, the width of the inflatable part must be in the neighbourhood of 40% of the circumference of the arm.

One embodiment of an overlap detector is described in conjunction with FIG. 6. This means that a signal related to the circumference of the limb is readily available with sufficient precision for use in correcting the reading of systolic and diastolic pressures. This correction may be performed automatically by the implement in the DSP environment assisting the measurement. Alternatively, the DSP functions may alert the user to the fact that the range for normal measurement has been exceeded, it may propose a correction, or provide the raw measurement data, leaving the decision of how to handle the mismatch to the examining physician.

In FIG. 5 is shown the principle for selecting the microphone that provides the most significant signal related to the flow in the partly occluded artery 3. A number of microphones 140 are connected to a set of pre-amplifiers 20, and each amplified signal is brought to a processing unit 21, which performs digital signal processing by emulating functions comprising high frequency pre-emphasis means, strobing means for selecting each microphone signal, level detection means for each signal, storage means corresponding to each signal for the level of high frequency present, comparator means for comparing the level of a newly strobed signal with those stored, and selector means for taking the signal fulfilling the set criteria to a unit 22, in which it is made available to the ear and to a visual indication. In this conjunction electronic transmission of the signal for further processing may also occur. The unit 23 is a timing and synchronising unit which aids in the selection according to the set criteria by linking the measurements in unit 21 to other measurable quantities having a time function.

In FIG. 6 is shown one embodiment of a capacitive overlap detector. A number of fixed capacitor plates P1, P2, . . . Pn are disposed at one end of the cuff in a row in the longitudinal (peripheral) direction of the cuff. The capacitor plates are connected to taps in a series connection of resistors R1, R2, . . . Rn supplied with a high frequency current provided via a capacitive coupling consisting of further parallel plates C1, C2 to a suitable part of the shell. The ground connection to the other end of the series connection of resistors is shown as capacitor plates C5, C6. The row of capacitor plates cooperates with a sliding capacitor plate D disposed at the other end of the cuff and brought in parallel proximity during the closing of the strap. The sliding capacitor plate D is connected to a predetermined part of the shell via coupling capacitor plates C3, C4. This construction functions as a capacitively coupled potentiometer which provides a sufficiently linear output voltage V in dependence of the placement of the sliding capacitor plate D, and it falls within the tasks of the skilled person to design the precise configuration for any practical strap, its thickness and dielectric constant. The voltage may be determined as the real part of the complex voltage V when the impedance Z of the resistor-capacitor network is fed by a current I. The cuff and strap (as opposed to the shell) are disposable and/or autoclaveable parts, and hence all signal coupling is capacitive. Preferably all capacitor plates are made in metal foil, however the high impedances involved makes the use of metallised plastic foil equally useful.

Signal processing means convert the output voltage to a value which is provided to the data processing means in order that a suitable correction may be obtained, preferably by accessing a table of corrections. If the circumference is outside the limits for the particular cuff, a warning can be given. It is also possible to suggest a correction for the measured blood pressure when the cuff width/circumference ratio differs from 0.4 (40%).

The equivalent circuit of the preferred embodiment of the system for determining degree of overlap is shown in FIG. 7. Provided that $Z_{load}$ is relatively high the current generator forces a constant current to flow in the loop, (Ci1 Rvar Co Ci2). The loop capacitance, the imaginary part of $Z_{loop}$, in the couplings are dependent of the formed geometry, area and distance between the plates. The loop resistance, the real part of $Z_{loop}$, is only dependent on the slider position, the overlap of the cuff ends, and thereby related to circumference. As the current is constant, the voltage across the current generator is proportional to the loop impedance. By determining the real part of the voltage, the part in phase with the current, the circumference can be expressed. If the sampling frequency is much higher than the frequency of the current, the calculation can be done by the built in microprocessor. However, to ensure that the imaginary impedance is on a reasonable level, compared to the real impedance, a relatively high frequency for the current is desirable. In order to keep the sampling frequency down the real part is extracted by by analog quadrature detection. The total circumference is expressed as: circumference=Xo+f(real (V))

The foregoing description of the specific embodiments will so fully reveal the general nature of the present invention that others skilled in the art can, by applying current knowledge, readily modify or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

The invention claimed is:

1. Apparatus for measuring blood pressure, comprising a generally tubular constrictable sleeve or cuff for a limb of a person, a source for fluid pressure, a detector for providing measurements of slowly varying static pressures in said sleeve or cuff, and microphone means adapted for being arranged, in use, in proximity to an artery, wherein the cuff is at least partly enclosed in two essentially concave shell parts displaying a stiffness in an axial direction, said shell parts being openable against a restoring force, wherein the microphone means comprises a linear array of microphone elements disposed on a joint support which emulates a universal joint in one shell part essentially perpendicular to the longitudinal axis of such shell part and near the lower end; and wherein an inelastic strap attached to one shell part is provided to close a gap between the shell parts.

2. Apparatus according to claim 1, wherein signal selection means of the diversity reception type are used to select the microphone that provides the best signal-to-noise ratio.

3. Apparatus according to claim 1, wherein the microphone signal is amplified and made available to an electroacoustic converter for enabling listening to the signal.

4. Apparatus according to claim 3, wherein the signal is output via a built-in speaker in the apparatus.

5. Apparatus according to claim 3, wherein the signal is output via a wireless link to a receiver connected to earpieces adapted to be worn, in use, by an auscultating physician.

6. Apparatus according to claim 1, further comprising signal processing means for combining information derived from measurements of slowly varying static pressures with information from said microphone means in order to obtain a numerical value for a blood pressure.

7. Apparatus according to claim 1, wherein said sleeve or cuff is adapted to fit an leg of a person.

8. Apparatus according to claim 1, wherein the strap is provided with means locking to the other shell part in conjunction with the overlapping of said strap and said other shell part.

9. Apparatus according to claim 8, wherein the amount of overlap between the strap and the shell part is used as a circumference measure for correcting the reading of blood pressure.

10. An apparatus according to claim 9, wherein the overlap is measured capacitively between an electrode or a plurality of electrodes fixed to the cuff and an electrode or a plurality of electrodes fixed to the strap.

11. Apparatus for measuring blood pressure, comprising a generally tubular constrictable sleeve or cuff for a limb of a person, a source for fluid pressure, a detector for providing measurements of slowly varying static pressures in said sleeve or cuff, and microphone means adapted for being arranged, in use, in proximity to an artery, wherein the cuff is at least partly enclosed in two essentially concave shell parts displaying a stiffness in an axial direction, said shell parts being openable against a restoring force, wherein the microphone means comprises a linear array of microphone elements disposed on a joint support which emulates a universal joint in one shell part essentially perpendicular to the longitudinal axis of such shell part and near the lower end; and wherein the shells are fitted on hinge parts connected to handle parts operable by one hand.

12. Apparatus according to claim 11, wherein the shell parts are integral with the hinge parts, forming one continuous sheet of material.

13. Apparatus according to claim 12, wherein the continuous sheet of material assumes a generally frusto-conical shape in its closed state.

14. Apparatus according to claim 11, wherein mechanical actuating means fitted in proximity to the hinge parts compress one shell part towards the other during measurement.

15. Apparatus according to claim 14, wherein the mechanical actuating means comprises an air cylinder and levers.

16. Apparatus according to claim 14, wherein the mechanical actuating means comprises strings fitted near the inner side of each shell part and disposed perpendicular to the longitudinal axis of such shell part.

17. Apparatus according to claim 1, wherein, in addition to a stiffness in the longitudinal direction, the shell structure displays a resilience in the circumferential direction.

18. Apparatus according to claim 17, further comprising a hinge that is a continuous resilient part joining the shell parts.

19. Apparatus according to claim 1, wherein the constrictable sleeve or cuff forms an inner lining to the shell parts, providing an inflatable main air chamber.

20. Apparatus according to claim 1, wherein the constrictable sleeve or cuff forms an inner lining to the shell parts, providing an inflatable main air chamber, and wherein the strap is provided with air chambers disposed essentially perpendicular to the orientation of the shells and communicating with the main air chamber.

21. Apparatus for measuring blood pressure, comprising a generally tubular constrictable sleeve or cuff for a limb of a person, a source for fluid pressure, a detector for providing measurements of slowly varying static pressures in said sleeve or cuff, and microphone means adapted for being arranged, in use, in proximity to an artery, wherein the cuff is at least partly enclosed in two essentially concave shell parts displaying a stiffness in an axial direction, said shell parts being openable against a restoring force, wherein the microphone means comprises a linear array of microphone elements disposed on a joint support which emulates a universal joint in one shell part essentially perpendicular to the longitudinal axis of such shell part and near the lower end; and wherein joint support emulates a universal joint by means of a foam pad.

22. Apparatus according to claim 1, wherein joint support emulates a universal joint by means of a separate air chamber fitted between the cuff and the microphone array.

23. Apparatus according to claim 1, wherein said sleeve or cuff is adapted to fit an arm of a person.

* * * * *